United States Patent [19]

Carosino et al.

[11] Patent Number: 4,997,991
[45] Date of Patent: Mar. 5, 1991

[54] SYNTHESIS OF DIETHYNYLBENZENE

[75] Inventors: Lawrence E. Carosino; David C. Herak, both of Wilmington, Del.

[73] Assignee: Hercules Incorporated, Wilmington, Del.

[21] Appl. No.: 498,679

[22] Filed: Mar. 26, 1990

[51] Int. Cl.$^5$ ............................................... C07C 5/00
[52] U.S. Cl. .................................... 585/319; 585/409; 585/464
[58] Field of Search ........................ 585/319, 409, 469

[56] References Cited

U.S. PATENT DOCUMENTS

| | | | |
|---|---|---|---|
| 3,594,423 | 7/1971 | Relles | 585/319 |
| 3,696,158 | 10/1972 | Relles | 585/319 |
| 3,758,622 | 9/1973 | Watson | 585/319 |
| 4,120,909 | 10/1978 | Amirnazmi | 260/668 R |
| 4,665,246 | 5/1987 | Anderson | 585/319 |

OTHER PUBLICATIONS

84 Chem. Abstracts, 105119 (1976).
Journal of Organic Chemistry, 2489-2496, vol. 53, (1988).
Journal of Organic Chemistry, 2493-2494, vol. 47 (1982).

*Primary Examiner*—Patrick P. Garvin
*Assistant Examiner*—E. D. Irzinski
*Attorney, Agent, or Firm*—Mark Goldberg

[57] ABSTRACT

The invention provides an inexpensive synthesis process for preparation of diethynylbenzene monomers that are useful in the preparation of polyacetylenes. This process provides for the preparation of thermally sensitive monomers in a one-pot reaction using readily available materials at low temperatures in an environment capable of absorbing large amounts of energy. Divinylbenzene is first brominated and then dehydrobrominated with sodium hydroxide or potassium hydroxide preferably in the presence of a phase transfer agent followed by distillation to recover the diethylnylbenzene product.

16 Claims, No Drawings

SYNTHESIS OF DIETHYNYLBENZENE

This invention relates to a process for preparing diethynylbenzenes. More particularly, it relates to a "one-pot" process involving the bromination of divinylbenzene while controlling over-bromination, preferably followed by treatment with a phase transfer agent, dehydrobromination and then by recovery of the desired product. The diethynylbenzenes produced by the process of this invention can be polymerized to form polyarylacetylene molding compositions and thermoset resins prepared therefrom as shown in U.S. Pat. Nos. 4,070,333 and 4,097,460.

BACKGROUND OF THE INVENTION

It is known that ethynylbenzenes may be produced by means of a sequence of halogenation and dehydrohalogenation reactions. For example, phenylacetylene may be prepared by the addition of bromine to styrene to produce $\alpha,\beta$-dibromoethyl benzene followed by the removal of two molecules of hydrogen bromide from the dibromo compound by treatment with an alkali. A modification of this procedure involves the bromination of ethylbenzene. For example, the bromination of diethylbenzene followed by dehydrobromination with sodium hydroxide produced diethynylbenzene monomers. This process suffers from the disadvantage that more than twice as much bromine is required as in the present invention and half of that excess evolves as HBr that has to be recovered in addition to the bromide generated in the dehydrobromination step.

In U.S. Pat. No. 4,120,909 while ethynylbenzenes were prepared from methyl phenyl ketones, it was stated that a similar procedure could be used to prepare meta or para diethynylbenzene from the corresponding divinylbenzene or diethylbenzene as the starting material. However, these halogenation-dehydrohalogenation processes have been described as expensive, complicated and giving comparatively low yields of the desired products.

Some processes used chloroform as the solvent which, as a suspected carcinogen, is now all but banned from use in commercial processes. For example, A. S. Hay, in Volume 25 of the Journal of Organic Chemistry at page 637 (1960), disclosed a process for brominating commercial divinylbenzene in chloroform with the separation of its various components via molecular distillation. Molecular distillation is not a practical procedure for commercial applications and the use of chloroform presents environmental problems in the workplace.

N. N. Lebedev, et al. in 84 Chem. Abstracts 105109e (1976) discloses the use of "technical" divinylbenzene (52% of a mixture of meta and para divinylbenzene and 34% of a mixture of meta and para ethylstyrene) as a starting material. Chlorine in dimethyl formamide was used to halogenate the monomer, and potassium hydroxide in isopropanol was used to convert the chlorinated intermediate into diethynylbenzene, which was obtained in 45% yield. In the present invention, the use of a high purity grade of divinylbenzene (about 78% pure) is taught, with a much higher yield of diethynylbenzene.

More recently, Neenan et al. in Vol. 53, Journal of Organic Chemistry, 2489 (1988) discloses the reaction of 1,3-dibromobenzene with trimethylsilylacetylene (TMSA) using dichlorobis(benzonitrile)palladium, triphenylphosphine, and copper (I) iodide as catalyst. Their initial attempt to distill the diethynylbenzene by this method resulted in an exothermic reaction and an explosion. Therefore, it was stated that these compounds should be distilled at high vacuum and at temperatures of less than 60° C. in well-shielded equipment. They note that the absence of an inexpensive route to produce the diethynylbenzene monomers has discouraged the full development of polyacetylenic aromatic compounds.

Polyarylacetylene resins have been the subject of extensive research leading to numerous patents because of their excellent properties. They are capable of being molded with little or no evolution of volatiles and can be cured simply by heating. They have good electrical properties and are stable to high temperatures. Furthermore, because of the high carbon yields produced upon their pyrolysis (85-90%) they are excellent precursors for carbon-carbon composites in ablative applications. For these reasons and others as well, resins of this type have been the object of investigation for many years. Attempts have been made to develop these resins as commercial materials, mainly by the General Electric Company and by Hercules Incorporated. However, their full commercial development has been discouraged by the absence of an inexpensive, safe route to the diethynylbenzene monomers as noted in the 1988 article by Neenan.

Now for the first time, an improved, inexpensive synthesis process for preparation of such diethynylbenzene monomers is provided. This process provides for the preparation of the thermally sensitive monomers in a one pot reaction using readily available materials at low temperatures in an environment capable of absorbing large amounts of energy. It further provides a process that produces a high yield of product with a significantly reduced requirement for bromine in the bromination phase of the process. In the present invention, divinylbenzene is first brominated and then dehydrobrominated, followed by distillation to recover the diethynylbenzene product. More specifically, a brominated divinylbenzene product is produced by continuously and simultaneously combining mixed isomers of divinylbenzene and bromine in a sulfolane solution wherein said divinylbenzene is present in a concentration not exceeding 5 percent by weight, wherein the temperature is between 0°-50° C., and wherein sufficient bromine is added to the reaction mixture to react with all olefinic unsaturation of the divinylbenzene. The quantity of bromine is not to be more than 10 percent more than an amount necessary to react with all of said olefinic unsaturations and the total amount of divinylbenzene added to the reaction mixture is between 20-50 percent by weight of the sulfolane solvent. The next step is to react the treated brominated divinylbenzene product with a dehydrobromination caustic agent such as sodium hydroxide or potassium hydroxide. An excess of the agent is added to total about 50-250 mole % more than the amount required to remove all organically bound bromine from the brominated divinylbenzene product as a corresponding halide salt. The caustic agent is added at a rate that maintains the temperature of the solution in the range of from about 20°-50° C. Addition of the caustic agent is continued until the excess of the agent is present and then the reaction with the caustic agent is completed by heating the dehydrobrominated product to a temperature between about 90° to about 100° C. for a period of about ½ to 4 hours. The excess dehydrobromination caustic agent and the halide salts are then removed and a layer is isolated comprising the sulfolane and diethynylbenzene. The final step in the process is to recover the diethynylbenzene from the isolated layer.

In an alternative procedure, all of the divinylbenzene is placed in the reaction vessel with the sulfolane solvent followed by gradual addition of bromine.

DETAILED DESCRIPTION OF THE INVENTION

The present invention provides a "one-pot" procedure for the synthesis of diethynylbenzene. The following equations summarize the chemistry of the invention.

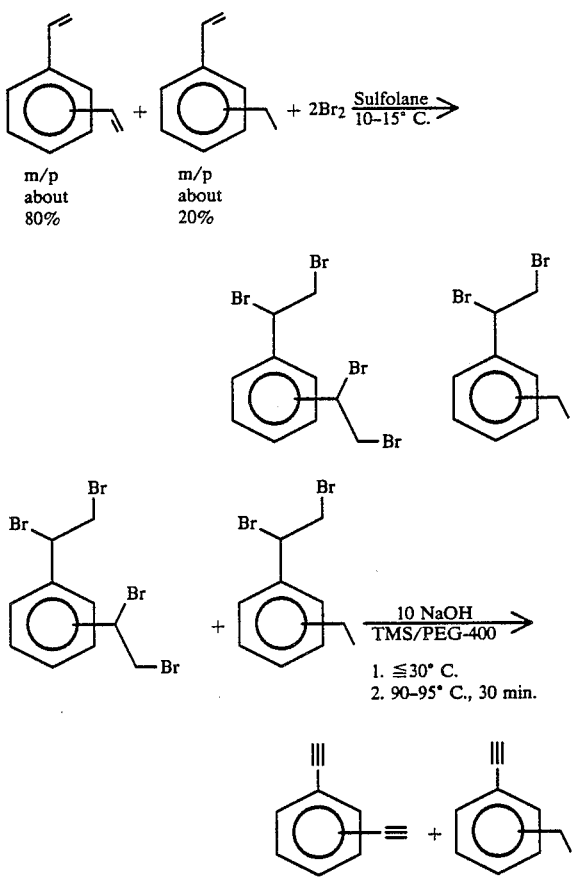

The starting material is divinylbenzene (DVB) that is available from the Dow Chemical Company in a high purity grade. An analysis of a typical sample of DVB showed the material to have the following composition:

| | | |
|---|---|---|
| Divinylbenzene | 79% | meta 54.7% |
| | | para 25.2% |
| Ethylstyrene | 18.0% | meta 10.5% |
| | | para 7.5% |
| Other | 2.1% | |

For the purposes of this invention, the commercial divinylbenzene employed should be between 50% to 80% of a mixture of meta and para isomers of divinylbenzene and preferably 75-80% divinylbenzene. The commercial divinylbenzene contains ethylstyrene and other impurities.

The reaction of bromine with divinylbenzene can be carried out by the addition of liquid bromine (Br) to the divinylbenzene in sulfolane solvent (tetramethylene sulfone, produced by Phillips Petroleum Company). When carried out in the laboratory on a small scale (5 liters or less) yields of diethynylbenzene in the range of 70–75% are obtained. The reaction is conveniently carried out at about 25 wt. % concentration divinylbenzene to solvent at 0°–50° C. To achieve higher productivity, this concentration may be as high as 40% by weight, but control of agitation and temperature become more difficult requiring an extended bromination period. For most purposes, the concentration of divinylbenzene will be limited to about 30% by weight.

The preferred concentration of bromine can be calculated from the concentration of olefinic unsaturation of the DVB monomer (0.65 ml Br per gram of DVB; the density of Br at normal room temperature is 3.06 g/ml). This leads to about 2% excess bromine in the reaction mixture. Large excesses of bromine are to be avoided since in the subsequent dehydrobromination step, excess bromine would be expected to form hypobromite after reaction with alkali. Hypobromite is an undesirable oxidizing agent and its presence is to be avoided or kept at the lowest possible levels. The final reaction mixture is a honey-colored to light red to amber viscous liquid.

It has further been found that when the reaction described herein is scaled up, a decrease in yield of the diethynylbenzene product is observed. It has been found that the yield is increased by maintaining a low concentration of divinylbenzene monomer and having a small percent excess bromine present throughout the course of the reaction. The reaction upon addition of bromine to divinylbenzene is instantaneous, but is accompanied by a steady low level elimination of HBr. The bromination reaction may be carried out at from 0° C. to 50° C. Preferably, the temperature is maintained in the range from 10°–15° C. to minimize over-bromination of DVB. If cooling is efficient, about three to four hours are required to carry out the bromination reaction and the polymerization side reaction is kept to a minimum.

The heat of reaction of the bromination step in sulfolane (20% concentration w/w at 20° C.) has been determined to be exothermic by 51–52 KCal./mole. The estimated adiabatic temperature rise for the entire amount of bromine is about 190° C. In large scale laboratory brominations, no more than a quarter of the total charge of bromine is ever placed in the addition funnel at one time. This precaution is taken to reduce the potential adiabatic temperature rise to about 45° C.

Dehydrobromination follows the bromination process described above. Either sodium hydroxide or potassium hydroxide is added to the reaction mixture to effect the dehydrobromination process. Other dehydrobromination caustic agents such as tetramethyl ammonium hydroxide or trimethylethanolammonium hydroxide (choline hydroxide) may also be used. When sodium hydroxide is used, it is about 50% aqueous and when potassium hydroxide is used it is about 45–60% aqueous. The total reaction mixture from the bromination step is preferably treated with a phase transfer agent at a concentration level of about 2% of the total weight of the brominated DVB plus sulfolane. Failure to add a phase transfer agent will result in a considerable reduction in the rate of dehydrobromination and a buildup in the amount of excess NaOH in the mixture with the potential for the onset of an exothermic reaction. However, since the dehydrobromination reaction will still proceed without the phase transfer agent, one can omit the phase transfer agent and either run the reaction at a higher temperature or for a longer period of time, or both.

The phase transfer agent shown in the examples herein is polyethylene glycol having the general formula HO—(CH$_2$CH$_2$O)$_n$—CH$_2$CH$_2$OH where n is an integer from 1–20. Other phase transfer agents that are useful in the dehydrobromination reaction include suitable quaternary ammonium compounds such as tricaprylylmethylammonium chloride, tetrabutylammonium hydrogen sulfate, and benzyltri-n-butylammonium bromide. The phase transfer agent is added in an amount so that it totals about 0.5 to 3.0% by weight of the reaction mixture including the weight of the caustic reagent added in the next step. The most preferred phase transfer agent is polyethylene glycol 400 (PEG-400; Dow Chemical Co.) having an average molecular weight of 400. The phase transfer agent remains in the recovered sulfolane phase and serves as a non-volatile distillation heel for the sulfolane distillation during diethynylbenzene recovery.

Dehydrobromination through addition of NaOH or KOH is carried out in two steps. The first step is exothermic and is carried out at 15°–30° C. (as shown in the following equation).

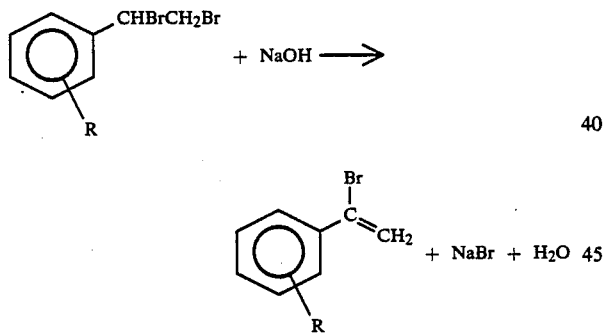

If the temperature is allowed to climb above about 30° C., a side reaction can occur which would result in a progressive decline in yield of diethynylbenzene. The side reaction involves hydrolysis of the vinylic bromide to a carbonyl function which would undergo further complex condensation reactions under strongly alkaline conditions. The removal of the first equivalent of hydrogen bromide from all of the brominated species in the mixture was found to be exothermic by 57.1 KCal./mole at 25° C. when KOH was the base. The heat of reaction with NaOH as the base would be expected to be less than measured for KOH.

After the first stoichiometric equivalent of NaOH has been added to effect the removal of one mole of HBr, the removal of the second mole of HBr becomes endothermic, and the system is heated to 90°–95° C. for thirty minutes to effect the following reaction.

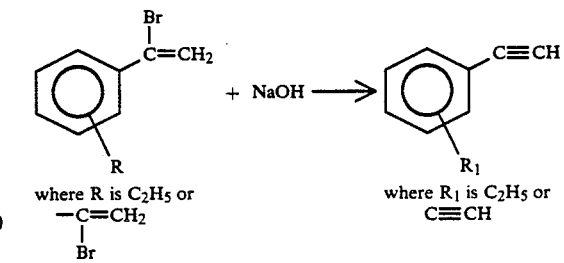

The reaction mixture undergoes profound color changes; from amber to magenta, to purple and eventually to dark brown. After the addition of about one-half of the necessary base to achieve dehydrobromination, the mixture becomes very viscous and has the appearance of an invert emulsion.

Heating for about thirty minutes at about 95° C. is sufficient to produce a reaction profile (by HPLC) that is virtually unchanged after three hours at that temperature. At this point the mixture is allowed to cool and at about 80° C. agitation is halted, the mixture easily undergoes phase separation and solid sodium bromide settles out The very dark upper layer consists of sulfolane with the diethynylbenzene and residual compounds.

The aqueous layer deposits crystalline sodium bromide. The total bromine analysis of the sulfolane layer amounts to only about 3% of the bromine used in the synthesis. More than 90% of the bromine used is converted to sodium bromide. Conversion of a large proportion of organic bromide to sodium bromide is essential to avoiding separation problems with the sulfolane layer arising from emulsion formation.

The final stage of the process is to recover the diethynylbenzene product. In the laboratory it has been found to be convenient to recover the product by steam distillation. The dried product from steam distillation is sufficiently pure for use in catalyzed polymerizations of the type described in U.S. Pat. No. 4,070,333 and U.S. Pat. No. 4,097,460 (previously mentioned). The ethynylbenzene recovery can also be accomplished by vacuum column distillation which affords a purer product. However, it is first necessary to remove soluble sodium bromide so it does not plug the column.

Furthermore, diethynylbenzene undergoes highly exothermic polymerization above 100° C. Conventional batch laboratory vacuum distillation of this product should be limited to amounts of 25 g. or less, with adequate safety precautions (see Neenan et al, J. Organic Chemistry, 53, 2489 (1988) previously cited).

After the layers have been allowed to separate and while the mixture is at about 80° C., the bottom layer, including most of the precipitated NaBr is removed by means of a vacuum-assisted dip tube. The lower layer and insoluble salts are almost completely drawn off into a filter flask by means of aspirator vacuum. Experience has shown that unless the salt-caustic layer is removed, the temperature of the subsequent steam distillation rises to as high as 120°–125° C. and slowly drops to about 108°–110° C. over the duration of the steam distillation. This is despite the inlet steam being at 100° C. Part of this exotherm is attributable to the heat of dilution of the residual concentrated caustic-NaBr layer.

Part of the reason for the prolonged character of this exotherm is that some of the diethynylbenzene monomer may be lost by polymerization. The exotherm can be reduced to a high of about 108° C., dropping to about 101°-103° C. at the end of the steam distillation by replacing the NaBr-caustic layer with water. It is critical to maintaining the highest possible yield of product to avoid metal ion contamination such as iron, nickel and other transition metals which may catalyze the unwanted polymerization of the acetylenic monomer during the steam distillation.

The steam distillate is condensed with ice-bath cooling and toward the end of this step solid para-diethynylbenzene tends to form on the walls. It is convenient for the purposes of separating the product layer to transfer the suspension to a jacketed vessel with a bottom drain. The slurry can be warmed to 40°-50° C., and the diethynylbenzene oil is then easily separated. The aqueous layer may be extracted with ethyl acetate or ethyl ether in a separatory funnel to recover a small additional amount of the diethynylbenzene product. Yields of product have been in the 70 to 75% range.

EXAMPLE 1

In Example 1 is described a laboratory procedure for producing diethynylbenzene using sodium hydroxide as the base for the dehydrobromination. A three-necked, five-liter, round-bottom flask was equipped with an air-driven Teflon paddle stirrer, a 250 ml vapor-bypass dropping funnel and a Y adapter provided with a pot thermometer, a gas inlet side arm and a condenser. The flask was cooled with an ice water bath.

The five-liter flask was charged with 1144 ml of anhydrous sulfolane (tetramethylene sulfone, Aldrich 99% pure). Then 470 grams (3.6 moles) of divinylbenzene (Dow Chemical Co., high purity, molecular weight of about 130 by bromine titration and gas chromatography analysis) was charged to the flask. The mixture was stirred and the flask was cooled to bring the temperature to about 10° C. An initial portion of 150 ml of liquid bromine was charged to the addition funnel and then added to the reaction flask dropwise at a rate to maintain the reaction temperature at a maximum of 15° C. A second portion of liquid bromine in the amount of 166 ml was charged to the addition funnel and added under the same conditions. A total of 316 ml of bromine was added (967 grams, 6.05 moles, based upon a density of 3.06 grams/ml. for bromine). The reaction of bromine with divinylbenzene was instantaneous and at the completion of the addition the reaction mixture was a light red-amber color.

Then 62.1 grams of Polyethylene Glycol 400 (Dow Chemical Co.) were added to the reaction mixture. The vapor-bypass funnel was rinsed out with 20% aqueous $NaHSO_3$ solution and water and was then charged with 250 ml of 50% aqueous NaOH solution. A total of 2884 grams (about 1900 ml) of 50% NaOH was used for the dehydrobromination, which constitutes about a 200 mole % excess of NaOH. When sufficient NaOH had been added to remove the first equivalent of HBr from the mixture of bromo compounds, the reaction temperature ceased to climb. The remainder of the NaOH was then added rapidly, and heat was applied to the reaction mixture to raise the temperature to about 95° C. for thirty minutes.

At this point the reaction was interrupted, the reactor was arranged for steam distillation, and the mixture allowed to cool to about 80° C. The mixture separated into a black organic upper layer and a colorless lower layer containing the excess NaOH and dissolved NaBr. Solid NaBr separated from solution during the cooling. The lower inorganic layer, including most of the insoluble salts, was drawn off with a vacuum siphon dip tube.

The bottom layer was then replaced with 1200-1300 ml of distilled water. The mixture was stirred and heated to over 90° C. and steam was passed into the mixture until about four liters of steam distillate had been obtained. The reactor was allowed to cool to room temperature. The dark upper layer of organic material was separated. The lower layer contained some dissolved salts and sulfolane. The steam distillate was composed of a yellow, oily, upper layer of diethynylbenzene and a hazy, lower, aqueous layer. This was separated in a jacketed resin kettle with a bottom drain. In this way the mixture could be heated with warm water to prevent para-diethynylbenzene from crystallizing. The recovered diethynylbenzene oil was dried over anhydrous sodium sulfate. On a five-liter scale, the reaction described in Example 1 affords about 300-350 grams of product or about a 70-75% yield.

EXAMPLE 2

In Example 2, diethynylbenzene was prepared from divinylbenzene using potassium hydroxide in place of sodium hydroxide.

A three-necked, five-liter, round-bottom flask, equipped with an air-driven teflon paddle stirrer, a 250 ml vapor-bypass dropping funnel and a Y adapter provided with a pot thermometer, a gas inlet side arm and a condenser was charged with 700 ml of tetramethylene sulfone (about 880 grams) (Aldrich, 99%) and 274 grams (2.11 mole) of divinylbenzene (Dow Chemical Co.). The mixture was stirred and cooled to 20° C. with an ice water bath. Liquid bromine was added dropwise over 1½ hours so as to maintain the temperature at 20°-28° C. with no loss of $Br_2$ vapor from the system. A total of 634 gms. (3.96 moles) of bromine was added, and the dark reaction mixture was allowed to stand overnight.

The mixture was stirred an additional two hours at room temperature, then 41.6 grams of polyethylene glycol (PEG-400; Aldrich) was added, (about 2% of the mixture by weight) and the stirred mixture was cooled to 1720 -18° C. To this was then added dropwise a 60% KOH solution (1375 grams of KOH pellets (85% KOH) in 916 grams distilled water, 20.9 moles KOH, 2290 grams of solution amounting to a 160 mole % excess) over about one hour while maintaining the temperature in the 18°-27° C. range with ice-bath cooling. The reaction exotherm is confined to the reaction of the first half of the KOH addition, which coincides with the removal of the first two moles of HBr. The removal of the second two moles of HBr leading to the acetylenic formation is endothermic.

The reaction mixture was then heated to 80° C. for two hours. The system was rearranged for steam distillation, and the reaction mixture was then steam distilled at about 110° C. for about 1½ hours to yield about two liters of distillate. The top layer of diethynylbenzene was separated (146.7 grams) and was dried over $Na_2SO_4$ in a dark bottle. The remainder of the steam distillate (aqueous layer) was extracted with 250 ml of ether and dried over $Na_2SO_4$. When evaporated, 2.1 grams of product was yielded.

Steam distillation was continued to yield another liter of steam distillate which was extracted with 250-350 ml of ether. The dried ether extract ($Na_2SO_4$) was evaporated to yield 11 grams of product.

The solution in the flask, upon standing overnight at ambient temperature, separated into two layers. The bottom aqueous layer was separated and discarded; the remainder was steam distilled to afford two more distillates of about one liter each. The first of these was extracted with 300 Ml of ether and after drying over Na₂SO₄, yielded 18.93 grams of oily product. The pot residue was discarded. The total of product fractions totalled 182.6 grams, corresponding to a yield of 68.7%. An analysis of the principal fraction by gas liquid chromatography produced the following results:

| Constituent | Aera Percent |
| --- | --- |
| 3-ethylphenylacetylene | 11.5 |
| 4-ethylphenylacetylene | 12.0 |
| m-diethynylbenzene | 48.5 |
| p-diethynylbenzene | 22.8 |
| Other | 5.3 |

EXAMPLE 3

In Example 3, diethynylbenzene was prepared from divinylbenzene using the same chemistry as in Example 1, but the addition method of bromine and divinylbenzene was altered. Instead of adding all the divinylbenzene to the pot initially, both the divinylbenzene and bromine were added in increments using dropping funnels. A jacketed, five-necked, 12-liter, round-bottom flask was equipped with a Teflon paddle stirrer, two 250 ml vapor-bypass dropping funnels, a pot thermometer, and a gas inlet tube. The flask was cooled using a refrigeration unit that pumped an ethylene glycol/water mixture through the jacket at about 5° C.

The 12-liter flask was charged with 1500 gm of anhydrous sulfolane (tetramethylene sulfone, Phillips 99.9% pure). Then 39 ml (36 gm) of divinylbenzene (Dow Chemical Co. high purity) was charged to the stirred reactor and the contents were cooled to 10° C.[1] The dropping funnels were charged with bromine and divinylbenzene. 25 ml of bromine were added to the flask dropwise at a rate to maintain the reaction temperature at 15° C. Then a 39 ml addition of divinylbenzene was made from the addition funnel to the reaction flask. Another 25 ml increment of bromine was added to the flask dropwise to maintain the temperature at 15° C. This procedure was repeated until 14 increments each of divinylbenzene and bromine had been added to the reactor. The total amounts added were 546 ml divinylbenzene (500 gm, 3.8 moles) and 350 ml bromine (1092 gm, 6.8 moles).

[1] It is necessary to add some DVB to the sulfolane (F.P.=27° C.) before cooling to 10° C. to avoid freezing of the sulfolane.

The reaction mixture was then dehydrobrominated using the same technique described in Example 1. Polyethylene Glycol 400 (61.4 gm) was added to the mixture and then a 50 wt. % NaOH solution was added. The temperature was maintained at 30° C. during the exothermic phase of the reaction by controlling NaOH addition and then raised to 95° C. for a 30 min. hold. The total mass of 50 wt. % NaOH added was 3200 gm, which represents a 200 mole % excess. The mixture was then cooled to 80° C., and the black organic upper layer was separated from the caustic layer and precipitated NaBr by decanting and using a separatory funnel.

The organic layer was then mixed with 500 ml of distilled water in a separate 12-liter flask which was equipped for steam distillation. The mixture was stirred and steam was passed into the mixture. The distillate was condensed and collected. The condensed distillate was composed of a yellow, oily, upper layer of diethynylbenzene and a hazy lower aqueous layer. This mixture was separated in a separatory funnel. The product collected weighed 362 gm, which represents a 76% yield. This yield was about 10-15% higher than for similar diethynylbenzene synthesis procedures in the 12-liter equipment where all the divinylbenzene was mixed with the sulfolane before any bromine was added, such as in Example 1.

What is claimed is:

1. A process for making diethynylbenzene as a mixture of isomers which comprises:

a. producing a brominated divinylbenzene product in a reaction mixture by in a gradual manner continuously and simultaneously combining mixed isomers of divinylbenzene with bromine in a sulfolane solvent wherein said divinylbenzene is present in a concentration not exceeding 5 percent by weight, wherein the temperature is between 0°-50° C., and wherein sufficient bromine is added to said reaction mixture to react with all olefinic unsaturation of said divinylbenzene; said bromine not to be more than 10 percent more than an amount necessary to react with all of said olefinic unsaturations and wherein the total amount of divinylbenzene added to the reaction mixture is between 20-50 percent by weight of the sulfolane solvent;

b. reacting said brominated divinylbenzene product with a dehydrobromination caustic agent wherein an excess of said agent is added to total about 50-250 mole % more than the amount required to remove all organically bound bromine as a corresponding halide salt from said brominated divinylbenzene product, and wherein said caustic agent is added at a rate that maintains the temperature of the solution in the range of from about 20°-50° C. and continuing addition of said caustic agent until said excess of the agent is present and then completing said reaction with said caustic agent by heating a dehydrobrominated product to a temperature between about 90° to about 100° C. for a period of about ½ to 4 hours;

c. removing said excess dehydrobromination caustic agent and said halide salts and isolating a layer comprising said sulfolane and diethynylbenzene; and d. recovering said diethynylbenzene from said isolated layer.

2. The process of claim 1 wherein said dehydrobromination caustic agent is selected from the group consisting of sodium hydroxide, potassium hydroxide, tetramethylammonium hydroxide and trimethylethanolammonium hydroxide.

3. The process of claim 2 wherein said caustic agent is selected from the group consisting of sodium hydroxide and potassium hydroxide.

4. The process of claim 1 wherein prior to the reaction of the brominated divinylbenzene with the caustic agent the brominated divinylbenzene is treated with a phase transfer agent.

5. The process of claim 4 wherein said phase transfer agent is selected from the group consisting of polyethylene glycol having a general formula HO—(CH₂CH₂O)-$_n$—CH₂CH₂OH where n is an integer from 1-20, tricaprylmethylammonium chloride, tetrabutylammonium hydrogen sulfate and benzyltri-n-butylammonium bromide.

6. The process of claim 5 wherein said phase transfer agent is polyethylene glycol having an average molecular weight of about 400 that is added in an amount that is about 0.5% to 3.0% by weight of the mixture including the weight of the caustic agent.

7. The process of claim 1 wherein the diethynylbenzene is recovered from said isolated layer through distillation.

8. The process of claim 1 wherein said divinylbenzene comprises between about 50% to about 80% of a mixture of meta and para isomers of divinylbenzene.

9. The process of claim 8 wherein said divinylbenzene comprises between about 75% to about 80% of a mixture of meta and para isomers of divinylbenzene.

10. The process of claim 1 wherein the total concentration of divinylbenzene in sulfolane is about 20% to about 30% by weight.

11. The process of claim 1 wherein a first equivalent of said caustic dehydrobromination agent is added while the temperature of said solution is maintained in the range from 20°–30° C.

12. The process of claim 1 wherein said dehydrobromination reaction is completed by heating said solution at about 95° C. for about 30 minutes.

13. The process of claim 2 wherein said caustic dehydrobromination agent is 50% aqueous sodium hydroxide.

14. The process of claim 2 wherein said caustic dehydrobromination agent is 45–60% aqueous potassium hydroxide.

15. The process of claim 1 wherein the amount of said dehydrobromination caustic agent is about 150 to about 200 mole % in excess of the amount required to achieve complete dehydrobromination of the brominated divinylbenzene.

16. The process of claim 1 wherein all of said mixed isomers of divinylbenzene is added to said sulfolane solvent followed by gradual addition of said bromine.

* * * * *